June 17, 1952 E. MARSH Plant Pat. 1,105
ROSE PLANT
Filed Dec. 13, 1949
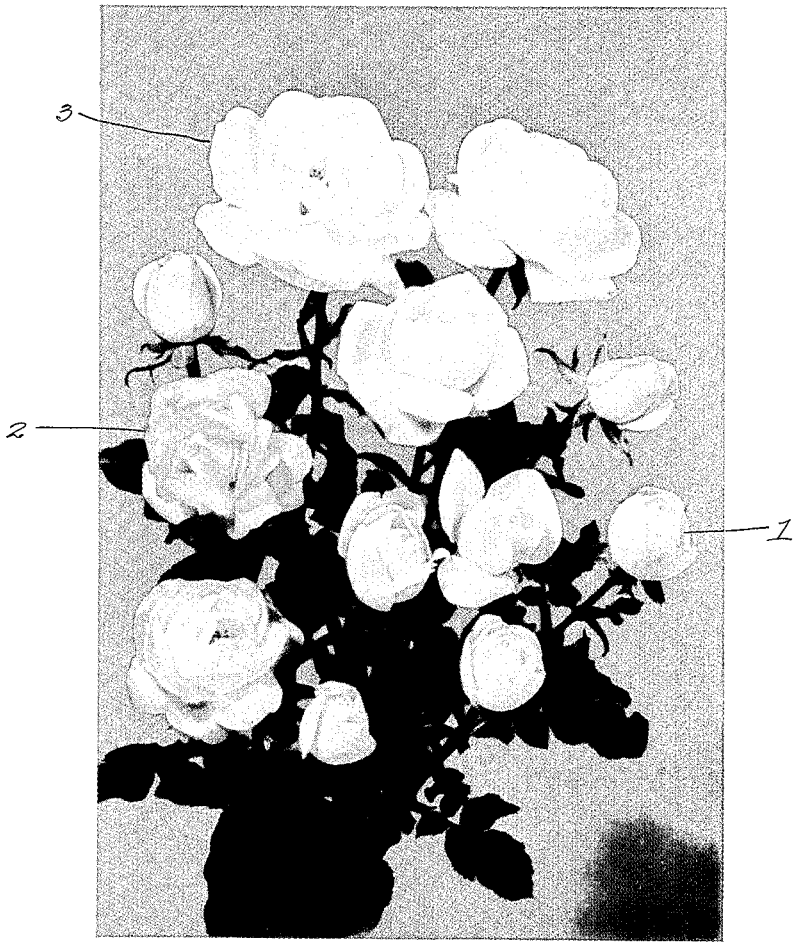
INVENTOR
Edward Marsh
By Wilfred E. Lawson
ATTORNEY Patented June 17, 1952

Plant Pat. 1,105

UNITED STATES PATENT OFFICE 1,105

ROSE PLANT

Edward Marsh, Pasadena, Calif.

Application December 13, 1949, Serial No. 132,685

1 Claim. (Cl. 47—61)

This invention relates to a new and distinct variety of rose plant which embodies novelty not only in the coloring of the flowers but in the general growth of the plant, which adapts it to certain garden and landscape uses for which other rose plants are not suitable.

The present plant has the following distinctive characteristics:

(1) A changing from day to day of the coloring of the petals from the first opening of the bud to the full blown stage.

(2) A changing of the outline or contour of the petals from day to day, begining with the first opening of the bud.

(3) The plant has a close or compact growth, forming a compact bush which is exceptionally suited for use as a hedge.

The foregoing characteristics are believed to be entirely new and novel and unlike any other rose plant known to me.

In the illustration are shown specimens of this new variety at different stages of development from the bud to the full blown flowers, the illustration also showing the novel features of the foliage.

In the pictured reproduction the flower illustrating the first day coloring and form is designated 1.

The reference numeral 2 designates the second day development of the flower.

The reference numeral 3 designates the third day devolpment of the flower when the same is about full blown.

The distinctive characteristics of this new rose plant are set forth more specifically in the following detailed description:

Type: Hardy; dwarf; outdoor; seedling; for garden decoration.

Class: Polyantha.

Parentage:

*Seed parent.*—Pinocchio (Plant Patent No. 484).

*Pollen parent.*—Mrs. E. P. Thom (unpatented).

Propagation: Holds its distinguishing characteristics through succeeding propagations by cuttings, grafting, budding and layering, which were made at Arcadia, California.

*Flower*

Locality where grown: San Fernando, California.

Flowers borne: Several in irregular cluster; on strong medium length stems.

Quantity of bloom: Free outdoors.

Continuity: Continuous.

Fragrance: Slight.

Bud:

*Peduncle.*—Medium length; medium weight; stiff; green; smooth.

*Before calyx breaks.*—*Size*—small. *Form*—globular with foliaceous appendages on the surface of the bud; with foliaceous parts extending beyond the tip of the bud equal to ¾ or more of its length.

*As first petal opens.* — *Size* — medium. *Form*—globular. *Color*—outside—sulphur yellow with streak of copper pink changing to shades of tangerine and copper orange; inside—yellow at first changing by hour to peach pink finally to red.

*Opening.*—Opens up well and is not affected by cold or heat.

Bloom:

*Size.*—When fully open—medium, 1½ inches to 2 inches.

*Petalage.*—Very double; from 16 to 60 petals arranged regularly; no one bud like another—each having different amounts of petals.

*Form.*—Cupped at first; petals remaining at first rolled inwardly; becoming later, at maturity, rolled outward.

Petals: Thick, with inside and outside satiny.

*Shape.*—Outside—oval. Intermediate—ovate. Inside—scalloped.

This description of a newly opened flower was made from a rose grown outdoors, in the month of April, 1947, at Pasadena, California. The petals on the second day the flower is open have the coloring altered so that the upper half of each petal shows salmon-pink while the lower half of the petal remains perfectly yellow.

On the third day the upper part of each petal has taken on a copper-red coloring while the lower half of each petal is and remains a pale yellow.

*Behavior.*—Persist; color deepens in cold weather and lightens in hot weather.

*Flower longevity.*—On bush in garden 7 days in month of April; cut roses, grown outdoors, kept at living-room temperatures 7 days in month of April.

*Reproductive organs*

Stamens: Very many; partly about pistils.

Filaments: Short, brown; many, with anthers.

Anthers: Very small; yellow; open at various times.

Pollen: Sparse, yellow.

Pistils: Very many.
Styles: Even; bunched.
Stigma: Green.
Ovaries: All enclosed in calyx.
Hips: Short, gourd-shaped, green, smooth; walls thin, fleshy.
Sepals: Permanent; long; spear-shaped.
Seeds: Very few; small.

*Plant*

Foliage:

*Leaves.*—Compound of 5 leaflets; very abundant.

*Leaflets.*—Ovoid, margin serrate.

*Color.*—*Mature*—upper surface dark green. Undersurface light green, tipped in purple and brown. *Young*—upper surface dark green. Undersurface light green, tipped in red.

*Rachis.*—(The supporting stem of the compound leaf)—heavy. Upper side—hairy. Under side—smooth.

*Stipules.*—Short, with short points, turning out at an angle of less than 45°, recurved toward the stem.

*Disease.*—Resistant to mildew, blackspot.

Growth:

*Habit.*—Dwarf, bushy, much branched.

*Growth.*—Free.

*Canes.*—Light.

*Main stems.*—Gray. Thorns—many; short, straight. Prickles—none. Hairs—none.

*Branches.*—Dull green. Thorns—many; medium; straight and hooked upward; with long narrow base. Prickles—none. Hairs—none.

*New shoots.*—Bright green. Thorns—several; short, straight; with short narrow base. Prickles—none. Hairs—none.

The plant is a bush type and attains a height of about two feet.

A distinguishing feature of the plant is the compact or close growth of the foliage.

Because of the compact or close form of its growth the present rose plant is well suited to use as a hedge.

I claim:

A new and distinct variety of rose plant as described and illustrated, characterized as to novelty by the compactness of its foliage wherein the leaves have a deep green color and in new growth have red tips; by the production of flowers which, upon the breaking of the calyx, show for the first day petals of sulphur yellow tinged with pink opening to shades of tangerine and copper orange and on the second day have their upper halves salmon pink and their lower halves remaining yellow and on the third day have their upper halves copper red and their lower halves a pale yellow; and by having an average height of about two feet whereby the plant is particularly adaptable to use as a border or hedge plant.

EDWARD MARSH.

REFERENCES CITED

The following references are of record in the file of this patent:

UNITED STATES PATENTS

| Number | Name | Date |
|---|---|---|
| Pl. Pt. 245 | Bate | Apr. 20, 1937 |
| Pl. Pt. 312 | Byrum | Jan. 24, 1939 |
| Pl. Pt. 454 | Lammerts | Feb. 25, 1941 |
| Pl. Pt. 461 | Johnston | Mar. 18, 1941 |
| Pl. Pt. 596 | Mallerin | July 13, 1943 |
| Pl. Pt. 874 | Verschuren | Sept. 20, 1949 |
| Pl. Pt. 885 | Swim | Oct. 25, 1949 |